United States Patent [19]
Harsanyi et al.

[11] Patent Number: 5,589,486
[45] Date of Patent: *Dec. 31, 1996

[54] N-HYDROXYALKYL-SUBSTITUTED 1,2,3,6-TETRAHYDRO-PYRIDINE AND PIPERIDINE DERIVATIVES

[75] Inventors: Kalman Harsanyi; Tibor Gizur; Eva Agai-Csongor; Anna Kallai-Sohonyai; Marta Kapolnas-Pap; Eva Csizer; Bela Hegedüs; Laszlo Szporny; Bela Kiss; Egon Karpati; Eva Palosi; Zsolt Szombathelyi; Adam Sarkadi; Aniko Gere; Mihaly Bodo; Katalin Csomor; Judit Laszy; Zsolt Szentirmai; Erzsebet Lapis; Sandor Szabo, all of Budapest; Peter Bod, Gyömro; Attila Csehi, Göd, all of Hungary

[73] Assignee: Richter Gedeon Vegyeszeti Gyar Rt., Budapest, Hungary

[*] Notice: The term of this patent shall not extend beyond the expiration date of Pat. No. 5,225,416.

[21] Appl. No.: 244,867

[22] PCT Filed: Dec. 1, 1992

[86] PCT No.: PCT/HU92/00050

§ 371 Date: Jan. 17, 1995

§ 102(e) Date: Jan. 17, 1995

[87] PCT Pub. No.: WO93/11107

PCT Pub. Date: Jun. 10, 1993

[30] Foreign Application Priority Data

Dec. 2, 1991 [HU] Hungary ................ 3747/91
Jun. 9, 1992 [HU] Hungary ................ 3747/91

[51] Int. Cl.[6] ............ A61K 31/445; C07D 211/22
[52] U.S. Cl. ............ 314/317; 514/277; 514/319; 514/327; 514/345; 546/205; 546/217; 546/240; 546/241; 546/285; 546/291; 546/344
[58] Field of Search ............ 546/205, 240, 546/217, 241, 285, 291; 514/344, 319, 317, 327, 277, 345

[56] References Cited

U.S. PATENT DOCUMENTS 3,209,006  9/1965  Wragg et al. ............ 514/327
3,922,266  11/1975  Katsube et al. ............ 514/327
3,936,468  2/1976  Yamamoto et al. ............ 514/327
4,012,515  3/1977  Katsube et al. ............ 546/217
4,254,129  3/1981  Carr et al. ............ 546/239
4,254,130  3/1981  Carr et al. ............ 546/237
5,225,416  6/1993  Gizur et al. ............ 514/277

FOREIGN PATENT DOCUMENTS 757994    12/1970  Belgium .
0490560A1  6/1992  European Pat. Off. .
WO91/08200  6/1991  WIPO .

OTHER PUBLICATIONS

Arimura et al. "Butyronaphthones as psycho drugs" CA 74:99715 (1971).

Ibanez–Paniello "Reduction of p,p'-difluoro-benzophenone" CA 80:70478 (1974).

Primary Examiner—Ceila Chang
Attorney, Agent, or Firm—Herbert Dubno; Jonathan Myers

[57] ABSTRACT

The invention relates to novel N-hydroxy-substituted 1,2,3,6-tetrahydropyridine and piperidine derivatives of the formula

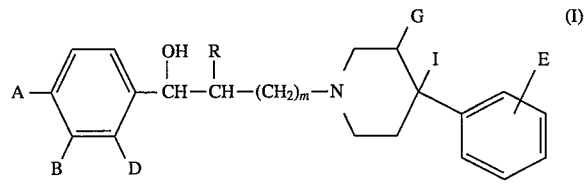

wherein A, B, D, E, G, I and R are as defined in the specification,
m is 0, 1 or 2, with the proviso that:
m is 0 or 2, or both G and I are hydrogen, when A is benzyl or halogen-monosubstituted benzyl group; and
m is 1, when A is 2-picolyl, as well as their pharmaceutically acceptable acid addition salts. The compounds of formula (I) are useful for enhancing the tolerance of mammals (including man) against hypoxic and/or ischaemic states as well as for treating the degenerative and functional disturbances arising from hypoxic and/or ischaemic results.

8 Claims, No Drawings

N-HYDROXYALKYL-SUBSTITUTED 1,2,3,6-TETRAHYDRO-PYRIDINE AND PIPERIDINE DERIVATIVES

FIELD OF THE INVENTION

The invention relates to novel N-hydroxyalkyl substituted 1,2,3,6-tetrahydropyridine and piperidine derivatives, to processes and intermediates for their preparation, to pharmaceutical compostions containing them and to their medical use.

BACKGROUND OF THE INVENTION

International Patent Application PCT/HU90/00076 describes tetrahydropyridine derivatives structurally related to the compounds of the invention which are said to have antiamnesic activity. In contrast to the present compounds, however, said compounds can be considered as β- or τ-amino ketone compounds the nitrogen atom of which is closed as a ring member into said substituted tetrahydropyridine ring.

The invention relates to novel, therapeutically active N-hydroxyalkyl-substituted 1,2,3,6-tetrahydropyridine and piperidine derivatives of the formula

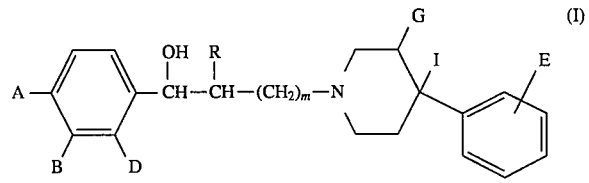

wherein
A is hydrogen or halogen; alkoxy; cyano; phenyl; phenyl monosubstituted by halogen; benzyl; benzyl monosubstituted by halogen; 2-phenylethyl monosubstituted by halogen on the phenyl moiety; or 2-picolyl group;
B is hydrogen; alkoxy or nitro;
D is hydrogen, halogen; or alkoxy; or
B and D together are a —CH=CH—CH=CH— group;
R is hydrogen; alkyl or phenyl;
G is hydrogen;
I is hydrogen or hydroxy; or
G and I together are a single chemical bond;
E is for hydrogen, halogen, alkoxy or trifluoromethyl; and
m is 0, 1 or 2,
with the proviso that:
m is 0 or 2, or both G and I are hydrogen, when A is benzyl or halogen-monosubstituted benzyl; and
m is 1, when A is 2-picolyl,
as well as their acid addition salts.

Alkyl group as used herein either in itself or as a moiety of another group, is a straight or branched chain saturated hydrocarbon group containing 1–10 carbon atoms such as methyl, ethyl, n- and isopropyl, n-, o-, sec- and tert-butyl groups as well as the various pentyl, hexyl, heptyl, octyl, nonyl and decyl groups. $C_{1-6}$alkyl groups are preferred, $C_{1-4}$alkyl groups are more preferable and methyl group is particularly favorable.

Halogen may mean fluorine, chlorine, bromine or iodine.
The following compounds are particularly preferred:

1-[4-(4-chlorobenzyl)phenyl]-2-(4-phenyl-1,2,3,6-tetrahydro-1-pyridyl)ethanol,
1-[4-(4-chlorobenzyl)phenyl]-3-(4-phenyl-1-piperidyl)propanol,
1-[4-(4-chlorobenzyl)phenyl]-4-(4-phenyl-1,2,3,6-tetrahydro-1-pyridyl)butanol,
3-[4-(4-fluorophenyl)-1-piperidyl]-1-(1,1'-biphenyl-4-yl)propanol,
3-[4-(4-chlorophenyl)-1,2,3,6-tetrahydro-1-pyridyl]-1-(2,4-dichlorophenyl)propanol.

The present invention also relates to a pharmaceutical composition for treating conditions selected from hypoxia and ischaemia comprising an amount of a compound of formula (I) or a pharmaceutically acceptable acid addition salt thereof effective in treating such conditions and a pharmaceutically acceptable carrier.

Furthermore, the present invention also relates to a process and intermediates for the preparation of the compounds of formula (I), as well as acid addition salt thereof.

Additionally, the present invention relates to a process for the preparation of pharmaceutical compositions comprising a compound of formula (I) or a pharmaceutically acceptable acid addition salt thereof.

The present invention also relates to a method of treatment, which comprises administering a therapeutically effective amount of a compound of formula (I) or a pharmaceutically acceptable acid addition salt thereof to a mammal (including man) for strengthening its tolerance against hypoxic and/or ischaemic conditions as well as for treating degenerative and functional disturbances arising from hypoxic and/or ischaemic insults.

Surprisingly, it has been found that the compounds of formula (I) are capable to protect the brain from the cognitive function-injuring effect of various harmful conditions, e.g. hypoxia and/or ischaemia; or they are useful to enhance the tolerance against hypoxic and/or ischaemic conditions, respectively as well as to treat degenerative and functional disturbances arising from hypoxic and ischaemic insults.

The biological effects of compounds according to the invention are hereinafter illustrated by using the following test methods.

Male CFLP mice (from the Hungarian stock LATI) weighing 24–26 g each and spontaneously hypertensive (SH) male rats weighing 160–180 g each, respectively were used in these investigations. The compounds to be tested were orally administered in a volume of 10 ml/kg one hour prior to starting the experiment.

ANTIHYPOXIC EFFECT IN MICE

1. The Cytotoxic Hypoxia Test

After a 1-hour pretreatment, the animals were intravenously injected with 5 mg/kg of potassium cyanide. Survival time was measured as an interval lasting from the administration of potassium cyanide to the last respiratory movement. In the groups consisting of 10 animals each treated with the compounds, the animals having a survival time longer by 30% than the average survival time of the placebo-treated group were considered to be protected. The $ED_{50}$ values (i.e. the doses being effective in 50% of the animals) were calculated from the percentage of the surviving animals by using probit analysis.

2. The Hypobaric Hypoxia Test

After a 16-hour starving and 1-hour pretreatment period, the animals were placed in a desiccator of 6 liters volume, where the pressure was decreased to 170 mmHg within 20 seconds. The survival time was registered from this time point up to the last respiratory movement of the animals.

Animals having a survival time longer by 30% than the average survival time of the control group were considered to be protected. The $ED_{50}$ values were calculated from the percentage of the animals protected by using probit analysis.

The results obtained are summarized in Table 1.

TABLE 1

| Compound (Sign) | Oral $ED_{50}$ (mg/kg) | |
| --- | --- | --- |
| | Cytotoxic hypoxia in mice | Hypobaric hypoxia in SH rats |
| A | 11.9 | 18.5 |
| B | 19.8 | 11.5 |
| C | 18.8 | 7.3 |
| D | 50.0 | 3.7 |
| E | >50.0 | 8.3 |
| Vincamine | 27.0 | 27.9 |
| Piracetam | 131.5 | 293.0 |

The chemical names of compound listed in Table 1 are as follows.
"A": 1-[4-(4-chlorobenzyl)phenyl]-2-(4-phenyl-1,2,3,6-tetrahydro-1-pyridyl)ethanol;
"B": 1-[4-(4-chlorobenzyl)phenyl]-3-(4-phenyl-1-piperidiyl)propanol;
"C": 1-[4-(4-chlorobenzyl)phenyl]-4-(4-phenyl-1,2,3,6-tetrahydro-1-pyridiyl)butanol;
"D": 3-[4-(4-fluorophenyl)-1-piperidiyl]-1-(1,1'-biphenyl-4-yl)propanol; and
"E": 3-[4-(4-chlorophenyl)-1,2,3,6-tetrahydro-1-pyridyl]-1-(2,4-dichlorophenyl)propanol.

Various forms of hypoxia were used for investigating the compounds. The functional disorganization and destruction of cells and death, respectively in otherwise healthy mice are caused by a decrease in the oxygen-saturation of haemoglobin in the hypobaric hypoxia and the inhibition of the mitochondrial respiratory enzyme in the cytotoxic hypoxia. Spontaneously hypertensive (SH) rats are more sensitive against hypoxic conditions than normotensive animals; similarly, patients suffering from hypertension have a less chance of survival after hypoxic injuries.

Vincamine [chemically (+)-14β-hydroxy-14α-methoxycarbonyl-14,15-dihydroeburnamenine] and piracetam (chemically 2-oxo-1-pyrrolidinylacetic acid amide) were used as reference drugs. Vincamine increases the oxygen supply (vasodilatory effect) and modulates the metabolic processes of brain (cerebroprotective effect) whereas piracetam improves mainly the adaptation ability of the brain in pathologic states.

The antihypoxic effect of vincamine is most pronounced in cytotoxic hypoxia and in addition, it has a prominent tolerance-enhancing action in hypobaric hypoxia. Essentially, piracetam exerts its effect in the same two tests.

The compounds according to the invention are more active in both tests in comparison to the reference drugs. It is particularly favorable that the antihypoxic effect is strongest in spontaneously hypertensive animals, which is a substantial therapeutical advantage under pathologic conditions.

The antihypoxic effect of compound "A" is the most favorable, since its effects are the same in the various tests of hypoxia and it is 2- or 3-times as effective as vincamine.

ACUTE TOXICITY STUDY IN MICE

OF-1 mice of either sex weighing 19–21 g were used. The test compound was administered through a catheter inserted into the stomach. A series of solutions was prepared, the concentrations were chosen to give a constant dosage volume of 0.1 ml/10 g. The observation time after the treatment was 72 hours. The $LD_{50}$ value was calculated according to Litchfield and Wilcoxon from six dose responses (maximal dose 1000 mg/kg p.o., n=10).

| Compound | $LD_{50}$ (mg/kg p.o.) |
| --- | --- |
| A | >1000 |
| E | >1000 |
| B | 697 |

The active agents of formula (I) can be formulated in pharmaceutical compositions by mixing them with non-toxic, inert, solid or liquid carriers and/or auxiliaries commonly used in the therapy for parenteral or enteral administration. Useful carriers are e.g. water, gelatine, lactose, starch, pectin, magnesium stearate, talc, vegetable oils such as peanut oil, olive oil and the like. The active agent can be formulated in any usual pharmaceutical composition, particularly solid composition, e.g. rounded or edged tablet, dragée or capsule such as gelatine capsule, pill, suppository and the like. The amount of the solid active ingredient may be varied within a broad range in a dosage unit of the composition (tablet, capsule, one unit of the formulated solution and the like), preferably it is between about 25 mg and 1 g. Optionally, these compositions may also contain other commonly used pharmaceutical auxiliaries, e.g. stabilizers, preservatives, wetting agents, emulsifying agents and the like. The compositions can be prepared in a known manner, e.g. by sieving, mixing, granulating and compressing the components in the case of solid compositions. The compositions may be subjected to other usual operations of the pharmaceutical technology, e.g. sterilization.

The dose to be used may be varied between wide limits depending on the body-weight and responsiveness of the person or animal to be treated, as well as on the severity of the state to be influenced, frequency and route of administration; however, the suitable dose can easily be determined by a physician skilled in the art.

The proposed daily doses of the active compounds of the invention for oral or enteral administration to the subject for the treatment of the conditions referred to above are between 0.1 to 50 mg of the active ingredient per kg body weight; however, this limit may be exceeded depending on the severity of the pathological state to be treated since the toxicity of the compounds of the invention is low. The daily dose of the active compound may be administered once or in subdoses to the patient to be treated.

According to an other aspect of the invention, there is provided a process for the preparation of compounds of the formula (I), which comprises treating an oxo derivative of the formula

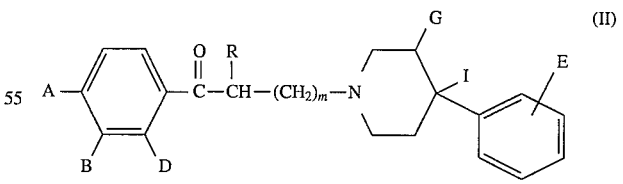

or an acid addition salt thereof with a reducing agent in an organic solvent and then, if desired, converting the obtained N-hydroxyalkyl-substituted 1,2,3,6-tetrahydropyridine or piperidine derivative of formula (I), wherein A, B, D, R, G, I, E and m are as defined above, to an acid addition salt thereof by reacting it with a mineral or organic acid.

Useful reducing agents for this purpose are complex metal hydrides, preferably sodium borohydride, though this reduction can also be accomplished e.g. by means of the Meerwein-Ponndorf-Verley reduction [Ann. Chem. 444, 221 (1926); Angew. Chem. 39 138 (1926)], e.g. by using an aluminium alkoxide in isopropanol medium.

The reduction of the oxo derivatives of formula (II) by sodium borohydride is preferably carried out in such a way that an acid addition salt of a compound of formula (II) is used as starting substance and the base is liberated in situ in the reaction medium. The reduction is accomplished in a lower alcohol or in the mixture of such an alcohol and water. In order to make the reaction complete, the reducing agent is employed in an excess or the temperature of the reaction is elevated to the boiling point in the final period.

The product obtained is isolated by filtration or extraction. It is suitable to dilute the reaction medium with water for completing the precipitation of the product. When extraction is used, a part of the alcohol is evaporated, then the reaction mixture is diluted with water and the product is extracted into a water-immiscible hydrocarbon, chlorinated hydrocarbon, ethyl acetate or ether. The final product may be purified by recrystallization. If desired, the compounds of formula (I) obtained in the base form can be converted to their acid addition salts by reacting them with an organic or inorganic acid for the salt formation in a known way. Hydrochloride salts are preferred.

The oxo compounds of formula (II) and their addition salts are also novel. These compounds can advantageously be prepared from hydrogenated pyridine derivatives of the formula

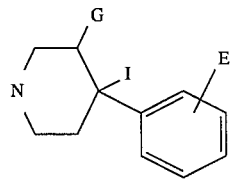

(III)

as starting material by either of two methods, which comprises
a) alkylating a compound of formula (III) with a halogenated ketone of formula

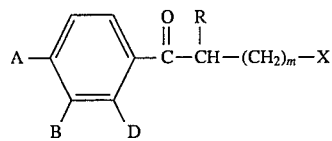

(IV)

wherein X is halogen, preferably chlorine or bromine, to obtain compounds of formula (II), wherein m is 0 or 2; or
b) reacting a compound of formula (III) with an acetophenone or propiophenone of formula

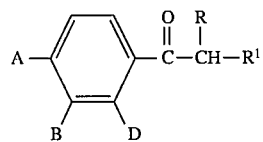

(VI)

wherein $R^1$ is hydrogen or methyl, in the presence of formaldehyde under conditions of the Mannich's reaction [Arch. Pharm. 250, 647 (1912)] to obtain compounds of formula (II), wherein m is 1.

A number of substances of formula (IV), e.g. phenacyl halides, α-bromopropiophenone [J. Chem. Soc. 125, 2343 (1924)], desyl bromide or 2-bromoacetophenone [Ann. 155, 68 (1870)] are known from the literature. Both latter compounds can be prepared by brominating the appropriate ketone; whereas the compounds of formula (IV), wherein m is 2 are mainly prepared by reacting an aromatic compound of formula

(V)

wherein B as well as D preferably are hydrogen, with 4-chlorobutyryl chloride under Friedel-Crafts condition.

Starting compounds of formula (V) are commercially available products.

Compounds of formula (VI) can be produced by reacting a compound of formula (V) with an appropiate acid chloride under Friedel-Crafts conditions. The ketone synthesis is not necessarily the final step of preparing the compounds of formula (VI); the formation of a substituent on the aromatic ring may also be the last step.

The invention is illustrated in detail by the following non-limiting Examples.

EXAMPLE 1

Preparation of
1-(4-Chlorophenyl)-3-[4-hydroxy-(4-chlorophenyl)-1-piperidyl]propanol To a solution containing 1.2 g (0.03 mol) of sodium hydroxide in 50 ml of an 50% by volume ethanol/water mixture, 12.41 g (0.03 mol) of 1-(4-chlorophenyl)-3-[4-hydroxy-(4-chlorophenyl)-1-piperidyl]propanone hydrochloride and then, over 1 hour 1.17 g of sodium borohydride are added. The suspension is heated at a temperature of 50° C. for 2 hours. After cooling down, the reaction mixture is filtered and washed with water to give 11.45 g of product, m.p.: 129°–132° C. After recrystallization of the latter product from 215 ml of acetonitrile, 9.1 g of title compound are obtained.

Analysis for $C_{20}H_{23}Cl_2NO_2$ (molecular weight 380.30) calculated: C 63.16; H 6.10; Cl 18,65; N 3.68%; found: C 62.94; H 6.17; Cl 18.41; N 3.48%.

EXAMPLE 2

Preparation of
3-[4-(4-Chlorophenyl)-1,2,3,6-tetrahydro-1-pyridyl]-1-(2,4-dichlorophenyl)propanol After adding 12.93 g (0.03 mol) of 3-[4-(4-chlorophenyl)-1,2,3,6-tetrahydro-1-pyridyl]-1-(2,4-dichlorophenyl)propanone hydrochloride to a solution of 1.2 g (0.03 mol) of sodium hydroxide in 50 ml of methanol, 1.17 g of sodium borohydride are portionwise added to the above mixture over 1 hour. After terminating the addition, the reaction mixture is boiled under reflux for 3 hours, then the reaction mixture is poured into 150 ml of water. The major part of methanol is distilled off from the so-obtained oily precipitate, which is then twice extracted with 50 ml of ethyl acetate each. After evaporating the solvent, 12.3 g of evaporation residue are obtained to give a crystalline product on addition of 50 ml of diisopropyl ether. In this way 8.32 g of title product are obtained, which is recrystallized from 28 ml of isopropanol to obtain 6.3 g of title compound, m.p.: 96°–98° C.

Analysis for $C_{20}H_{20}Cl_3NO$ (molecular weight 396.74) calculated: C 60.54; H 5.08; Cl 26.81 N 3.53%; found: C 60.80; H 5.03; Cl 26.62; N 3.60%.

The compounds listed hereinafter are prepared as described above by using the appropriate propanone derivatives of formula (II) as starting materials. The hydrochloride salts are obtained by adding ethanolic hydrogen chloride solution to the corresponding base.

1) 1-[4-(4-Chlorobenzyl)phenyl]-2-(4-phenyl-1,2,3,6-tetrahydro-1-pyridyl)ethanol, yield 93.2%, m.p.: 135°–137° C.;
2) 1-[4-(4-chlorobenzyl)phenyl]-3-(4-phenyl-1-piperidyl)propanol, yield 93.8%, m.p.: 98°–101° C.;
3) 1-[4-(4-chlorobenzyl)phenyl]-4-(4-phenyl-1,2,3,6-tetrahydro-1-pyridyl)butanol, yield 78.5%, m.p.: 108°–111° C.;
4) 3-[4-(4-fluorophenyl)-1-piperidyl]-1-(1,1'-biphenyl-4-yl)propanol, yield 90.7%, m.p.: 129°–132° C.;
5) 1-phenyl-2-[4-(3-trifluoromethylphenyl)-1,2,3,6-tetrahydro-1-pyridyl]ethanol, yield 80.5%, m.p.: 188°–190° C.;
6) 3-[4-(4-chlorophenyl)-1,2,3,6-tetrahydro-1-pyridyl]-2-methyl-1-phenyl-propanol, yield 80.9%, m.p.: 103°–105° C.;
7) 1-(4-chlorophenyl)-3-[4-(4-chlorophenyl)-1,2,3,6-tetrahydro-1-pyridyl]propanol, yield 82.8%, m.p.: 154°–155° C.;
8) 1-(4-chlorophenyl)-3-[4-(4-chlorophenyl)-1,2,3,6-tetrahydro-1-pyridyl]-2-methylpropanol, yield 84.0%, m.p.: 110°–112° C.;
9) 1-(4-chlorophenyl)-2-[4-(4-chlorophenyl)-1,2,3,6-tetrahydro-1-pyridyl]ethanol, yield 60.4%, m.p.: 152°–153° C.;
10) 3-[4-(4-chlorophenyl)-1,2,3,6-tetrahydro-1-pyridyl]-1-(3-methoxyphenyl)propanol, yield 87.4%, m.p.: 100°–102° C.;
11) 1-(4-chlorophenyl)-3-[4-(4-chlorophenyl)-1-piperidyl]propanol, yield 84.7%, m.p.: 152°–154° C.;
12) 1-(4-chlorophenyl)-3-[4-(4-fluorophenyl)-1-piperidyl]propanol, yield 70.5%, m.p.: 108°–110° C.;
13) 1-(4-chlorophenyl)-3-(4-phenyl-1,2,3,6-tetrahydro-1-pyridyl)propanol, yield 74.1%, m.p.: 141° C.;
14) 1-(4-fluorophenyl)-3-[4-hydroxy-(4-chlorophenyl)-1-piperidyl]propanol, yield 93.4%, m.p.: 116°–118° C.;
15) 1-(2,4-dichlorophenyl)-3-[4-hydroxy-(4-chlorophenyl)-1-piperidyl]propanol, yield 78.8%, m.p.: 146°–148° C.;
16) 1-(2,4-dimethoxyphenyl)-3-[4-hydroxy-(4-chlorophenyl)-1-piperidyl]propanol, yield 69.2%, m.p.: 129°–130° C.;
17) 4-[4-(4-chlorophenyl)-1,2,3,6-tetrahydro-1-pyridyl]-1-(4-fluorophenyl)butanol, yield 90.1%, m.p.: 103°–105° C.;
18) 1-[4-(4-chlorobenzyl)phenyl]-4-[4-(4-chlorophenyl)-1,2,3,6-tetrahydro-1-pyridyl]butanol, yield 90.7%, m.p.: 104°–105° C.;
19) 1-(4-cyanophenyl)-3-[4-(4-chlorophenyl)-1,2,3,6-tetrahydro-1-pyridyl]propanol, yield 76.5%, m.p.: 117°–118° C.;
20) 1-{4-[2-(4-chlorophenyl)ethyl]phenyl}-3-(4-phenyl-1,2,3,6-tetrahydro-1-pyridyl)propanol, yield 83.1%, m.p.: 158°–160° C.;
21) 1-(4-cyanophenyl)-3-[4-(4-methoxyphenyl)-1,2,3,6-tetrahydro-1-pyridyl]propanol, yield 74.7%, m.p.: 144°–145° C.;
22) 1,2-diphenyl-3-[4-hydroxy-(4-chlorophenyl)-1-piperidyl]propanol, yield 68.7%, m.p.: 150°–151° C.;
23) 3-[4-(4-chlorophenyl)-1,2,3,6-tetrahydro-1-pyridyl]-1-[4-(2-picolyl)phenyl]propanol, yield 40.0%, m.p.: 129°–131° C.;
24) 3-[4-(4-chlorophenyl)-1,2,3,6-tetrahydro-1-pyridyl]-1,2-diphenylpropanol, yield 82.7%, m.p.: 135°–137° C.;
25) 3-[4-(4-chlorophenyl)-1,2,3,6-tetrahydro-1-pyridyl]-1-(4-methoxyphenyl)propanol, yield 82.9%, m.p.: 116°–118° C.;
26) 1-(1-naphthyl)-3-(4-phenyl-1,2,3,6-tetrahydro-1-pyridyl)propanol, yield 88.8%, m.p.: 93°–94° C.;
27) 3-[4-(4-chlorophenyl)-1,2,3,6-tetrahydro-1-pyridyl]-1-(1-naphthyl)propanol, yield 75.4%, m.p.: 122°–123° C.;
28) 3-[4-(4-chlorophenyl)-1,2,3,6-tetrahydro-1-pyridyl]-1-(2,4-dimethoxyphenyl)propanol, yield 54.7%, m.p.: 112°–114° C.;
29) 3-[4-(4-chlorophenyl)-1,2,3,6-tetrahydro-1-pyridyl]-1-(4-fluoro-3-nitrophenyl)propanol, yield 30.0%, m.p.: 154°–156° C.;
30) 1-[4-(4-chlorobenzyl)phenyl]-3-[4-(4-fluorophenyl)-1-piperidyl]propanol, yield 83.4%, m.p.: 94°–95° C.;
31) 1-(1,1'-biphenyl-4-yl)-3-(4-phenyl-1-piperidyl)propanol, yield 87.7%, m.p.: 99°–101° C.;
32) 3-[4-(4-chlorophenyl)-1,2,3,6-tetrahydro-1-pyridyl]-1-(4-fluorophenyl)propanol, yield 90.5%, m.p.: 130°–132° C.;
33) 1-[4-(4-chlorobenzyl)phenyl]-2-[4-(4-chlorophenyl)-1,2,3,6-tetrahydro-1-pyridyl]ethanol, yield 87.3%, m.p.: 149°–152° C.;
34) 1-(2,4-dichlorophenyl)-3-(4-phenyl-1,2,3,6-tetrahydro-1-pyridyl)propanol, yield 57.3%, m.p.: 103°–104° C.;
35) 1-(1,1'-biphenyl-4-yl)-2-(4-phenyl-1,2,3,6-tetrahydro-1-pyridyl)ethanol, yield: 68.8%, m.p.: 190°–197° C.;
36) 1-(1,1'-biphenyl-4-yl)-2-[4-(4-fluorophenyl)-1,2,3,6-tetrahydro-1-pyridyl]ethanol, yield: 76.9%, m.p.: 202°–207° C.;
37) 2-(4-phenyl-1,2,3,6-tetrahydro-1-pyridyl)-1-(4'-fluoro-1,1'-biphenyl-4-yl)ethanol, yield: 96.6%, m.p.: 207°–210° C.; and
38) 4-(4-phenyl-1,2,3,6-tetrahydro-1-pyridyl)-1-[4-(4-fluoro-benzyl)phenyl]butanol, yield: 76.2%, m.p.: 164°–167° C.

EXAMPLE 3

Preparation of Tablets a) Tablets weighing 150 mg, containing 5 mg of active ingredient each

|  | g |
| --- | --- |
| Active ingredient | 5 |
| Gelatine | 3 |
| Magnesium stearate | 2 |
| Talc | 5 |
| Potato starch | 40 |
| Lactose | 95 | b) Tablets weighing 300 mg, containing 50 mg of active ingredient each

|  | g |
| --- | --- |
| Active ingredient | 50 |
| Polyvidone | 6 |
| Magnesium stearate | 3 |
| Talc | 9 |
| Potato starch | 84 |
| Lactose | 148 |

After wet granulation, the powder mixture containing the ingredients given above under a) or b), respectively is compressed to tablets. Each tablet weighs 150 mg or 300 mg, respectively and contains 5 or 50 mg, respectively of active ingredient.

We claim:
1. A compound selected from the group consisting of:
   (a) 1-[4-(4-chlorobenzyl)phenyl]-2-(4-phenyl-1,2,3,6-tetrahydro-1-pyridyl)ethanol;
   (b) 1-[4-(4-chlorobenzyl)phenyl]-3-(4-phenyl-1-piperidyl)-propanol;
   (c) 1-[4-(4-chlorobenzyl)phenyl]-4-(4-phenyl-1,2,3,6-tetrahydro-1-pyridyl)butanol;
   (d) 3-[4-(4-fluorophenyl)-1-piperidyl]-1-(1,1'-biphenyl-4-yl)propanol; and
   (e) 3-[4-(4-chlorophenyl)-1,2,3,6-tetrahydro-1-pyridyl]-1-)2,4-dichlorophenyl)propanol; or a pharmaceutically acceptable acid addition salt thereof.

2. 1-[4-(4-chlorobenzyl)phenyl]-2-(4-phenyl-1,2,3,6-tetrahydro-1-pyridyl)ethanol or a pharmaceutically acceptable acid addition salt thereof as defined in claim 1.

3. 1-[4-(4-chlorobenzyl)phenyl]-3-(4-phenyl-1-piperidyl)-propanol or a pharmaceutically acceptable acid addition salt thereof as defined in claim 1.

4. 1-[4-(4-chlorobenzyl)phenyl]-4-(4-phenyl-1,2,3,6-tetrahydro-1-pyridyl)butanol or a pharmaceutically acceptable acid addition salt thereof as defined in claim 1.

5. 3-[4-(4-fluorophenyl)-1-piperidyl]-1-(1,1'-biphenyl-4-yl)propanol, or a pharmaceutically acceptable acid addition salt thereof as defined in claim 1.

6. 3-[4-(4-chlorophenyl)-1,2,3,6-tetrahydro-1-pyridyl]-1) 2,4-dichlorophenyl)propanol or a pharmaceutically acceptable acid addition salt thereof as defined in claim 1.

7. A pharmaceutical composition for treating disorders arising from hypoxia and/or ischaemia, which comprises as active ingredient a therapeutically effective amount of the compound of the formula (I) as defined in claim 1, or a pharmaceutically acceptable acid addition salt thereof in admixture with one or more pharmaceutically acceptable inert carriers.

8. A method for enhancing the tolerance of mammals against hypoxic and/or ischaemic states as well as for treating the degenerative and functional disturbances arising from hypoxic and/or ischaemic results, which comprises the step of administering to a mammalian subject to be treated a therapeutically effective amount of a compound of the formula (I) as defined in claim 1, or a pharmaceutically acceptable acid addition salt thereof alone or in the form of a pharmaceutical composition.

* * * * *